(12) United States Patent
Buck

(10) Patent No.: US 6,337,337 B1
(45) Date of Patent: Jan. 8, 2002

(54) METHODS FOR TREATING DISORDERS RESPONSIVE TO DHFR-INHIBITION

(75) Inventor: Carol J. Buck, 30 Brooks Bend, Princeton, NJ (US) 08540

(73) Assignee: Carol J. Buck, Princeton, NJ (US)

( * ) Notice: Subject to any disclaimer, the term of this patent is extended or adjusted under 35 U.S.C. 154(b) by 0 days.

(21) Appl. No.: 09/390,609

(22) Filed: Sep. 3, 1999

Related U.S. Application Data

(60) Provisional application No. 60/098,941, filed on Sep. 3, 1998.

(51) Int. Cl.$^7$ .................. A61K 31/065; A61K 31/045; A61K 31/05; A61K 31/025; A61K 31/015

(52) U.S. Cl. .................. 514/311; 514/726; 514/727; 514/732; 514/756; 514/766

(58) Field of Search .................. 514/766, 726, 514/727, 732, 756

*Primary Examiner*—Theodore J. Criares
(74) *Attorney, Agent, or Firm*—Matthews, Collins, Shepherd & Gould, P.A.

(57) ABSTRACT

A method for treating disorders responsive to DHFR inhibition is disclosed, wherein the disorders may include neoplastic diseases, rheumatoid arthritis, restenosis, multiple sclerosis, lupus, infections, and ectopic pregnancy. The inventive method comprises administering to a patient in need of treatment a therapeutically-effective amount of a composition comprising certain aromatic, primarily non-aliphatic, molecules that may be found in coal tar.

12 Claims, No Drawings

US 6,337,337 B1

METHODS FOR TREATING DISORDERS RESPONSIVE TO DHFR-INHIBITION

RELATED APPLICATIONS

This application claims the benefit of U.S. provisional application Serial No. 60/098,941 filed Sep. 3, 1998, the contents of which is incorporated herein by reference.

FIELD OF THE INVENTION

The invention relates to methods for treating disorders responsive to DHFR inhibition including neoplastic diseases, rheumatoid arthritis, restenosis, multiple sclerosis, lupus, infections, and ectopic pregnancy. The inventive method comprises administering to a patient in need of treatment a therapeutically-effective amount of a composition comprising certain aromatic, primarily non-aliphatic, molecules that may be found in coal tar.

BACKGROUND OF THE INVENTION

Coal tar formulations have been investigated for use in treatment of a variety of mammalian health disorders. For example, a non-aliphatic pyrimidine composition known as Liquor Carbonis Detergens (LCD), a by-product of coal tar distillation, has been established as effective in treating certain skin disorders, particularly psoriasis. See, e.g., U.S. Pat. No. 4,102,995 to Hebborn, "Tar Gel Formulation." Coal tar contains a number of aromatic compounds, e.g., representative constituents of LCD may include benzene, toluene, xylene, phenol, indene, creosol, chrysene, napthalene, methylnapthalenes, thianapthalene, quinolines, acenaphthene, dibenzofuran, fluorene, phenanthrene, anthracene, carbazole, fluoranthene, pyrene, and benzo(a) anthracene.

The inventor herein has extensively studied coal tar formulations, their constituents, and their use in the treatment of human conditions and disorders. U.S. Pat. Nos. 5,512,275 and 5,609,858 (which are incorporated herein by reference), issued to the present inventor and relate to the treatment of androgenic alopecia with use of LCD. U.S. application Ser. No. 08/953,362 filed by the present inventor on Oct. 17, 1997, "Coal Tar Formulations for the Inhibition of NADPH Synthesis for Therapeutic Applications" (hereinafter referred to as the '362 application), relates to use of LCD formulations in the treatment of cancer.

Rheumatoid arthritis is an autoimmune disease which causes chronic inflammation of the joints, the tissue around the joints, and other organs in the body. Autoimmune diseases occur when the body tissues are mistakenly attacked by its own immune system. The immune system is a complex organization of cells and antibodies designed normally to "seek and destroy" invaders of the body, particularly infections. Patients with these diseases have antibodies in their blood which target their own body tissues, where they can be associated with inflammation.

The joint inflammation of rheumatoid arthritis causes swelling, pain, stiffness, and redness in the joints. The inflammation of rheumatoid disease can also occur in tissues around the joints, such as the tendons, ligaments, and muscles. In some patients with rheumatoid arthritis, chronic inflammation leads to the destruction and deformity of the joints. When the disease is active, symptoms can include fatigue, lack of appetite, low grade fever, muscle and joint aches, and stiffness. During flares, joints become red, swollen, painful, and tender. This occurs because the lining tissue of the joint (synovium) becomes inflamed, resulting in the production of excessive joint fluid (synovial fluid). The synovium also thickens with inflammation (synovitis).

Two classes of medications are used in treating rheumatoid arthritis: fast-acting "first-line drugs," and slow-acting "second-line drugs." The first-line drugs, such as aspirin and cortisone (corticosteroids), are used to reduce pain and inflammation. Slow-acting second-line drugs include gold, methotrexate and hydroxychloroquine (PLAQUENIL), which is related to quinine. DHFR inhibition is the mechanism of action of the antifolate drug methotrexate (MTX) and it would be advantageous to provide alternatives to MTX in treating arthritis and other diseases due to its long-term toxicity which is known for shortening life-span expectancy.

SUMMARY OF THE INVENTION

The instant invention is based on applicant's discovery that formulations based on coal-tar and LCD constituents are useful in treating disorders responsive to DHFR inhibition, including rheumatoid arthritis, restenosis, multiple sclerosis, lupus, infections, ectopic pregnancy, and neoplastic diseases. Thus, summarily described, the invention comprises a method for treating disorders responsive to DHFR inhibition comprising administering to a patient an effective amount of a composition comprising a plurality of aromatic compounds found in coal tar and in particular, a plurality of compounds selected from the group consisting of acenapththene, methylnaphthalene, anthracene, benzo(a) anthracene, biphenyl, carbazole, chrysene, dibenzofuran, fluoranthene, fluorene, indene, napththalene, phenanthrene, pyrene and quinoline.

DETAILED DESCRIPTION OF THE INVENTION

Applicant incorporates by reference the entire contents of her '362 application, referenced above. It is known that dihydrofolate reductase (DHFR) catalyzes the NADPH-dependent reduction of 7,8-dihydrofolate (H2F) to 5,6,7,8-tetrahydrofolate (H4F) and is necessary for maintaining intracellular levels of H4F, an essential cofactor in the synthetic pathway of purines, thymidylate and several amino acids. DHFR inhibition is the mechanism of action of MTX and trimethoprin which are used to treat a wide range of diseases including many cancers, infections, rheumatoid arthritis, multiple sclerosis, and lupus. Applicant has discovered that compositions based on coal tar constituents are also useful in inhibiting DHFR production and thus, for treating diseases responsive to such inhibition.

It is believed the inventive compositions inhibit the transfer of the hydrogen ion to dihydrofolate reductase, thus preventing metabolism within the nucleus of tetrahydrofolate, which is required to carry one-carbon groups in the synthesis of purine nucleotidase and thymidylate. Neoplastic cells are more responsive than slower dividing normal cells to this resulting interference with DNA synthesis, repair, and cellular replication. The invention functionally replicates MTX. The method of DHFR inhibition, however, is believed to be a non-competitive binding, electron transport, or allosteric affect on NADPH, the cofactor reducing agent, rather than by competitive blocking.

The instant compositions may be used as an alternative to methotrexate. Methotrexate is an anti-inflammatory, antiallergic, and immunosuppresive medication. Methotrexate is indicated in managing selected adults with severe, active, classical or definite rheumatoid arthritis who have experienced adverse effects or insufficiently therapeutic responses from a trial of first-line therapy including full dose NSAIDs and usually a trial of at least one or more disease-modifying antirheumatic drugs. Methotrexate has gained popularity among physicians as an initial second-line drug for treating arthritis because of its effectiveness and relatively infrequent side effects. However, like other immunosuppresive medications, it can present risks, e.g., a depressed bone marrow function and anemia, a low white cell count, and low platelets counts. A low white count can increase the risk of infections, and a low platelet count can increase the risk of bleeding. Methotrexate also is effective in treating other disorders, e.g., it has been used to induce miscarriage in patients with ectopic pregnancy. It has been shown to be effective for systemic lupus erythematosus, especially in patients who are not improving with steroid therapy. Methotrexate has shown effectiveness in providing relief in patients with lupus and various forms of arthritis.

The invention may be used as an alternative to MTX in treating the above-referenced disorders and several types of cancer. Inventive compositions may be used as a single agent to treat cancers of the prostate, melanoma, lung, particularly squamous cell and small cell types, meningeal leukemia, gestational choriocarcinoma, chorioadenoma destruens, and hydatidiform mole. Other possible cancers include: breast, colon, bone, testicular, epidermoid cancers of the head and neck, advanced mycosis fungoides, and advanced stage non-Hodgkin's lymphomas.

One preferred composition for use in the inventive method is referred to herein as "OncoX." OncoX may be prepared through distillation of coal tar or it may be synthetically prepared as including the constituents of a coal tar formulation. The composition may be combined either by coal tar distillation or mixed from pure chemicals in a solution of DMSO which serves as a solvent. One advantageous formulation (percentage by weight) is set forth below:

| Compound | % by Weight |
| --- | --- |
| Acenapththene | 0.6 |
| 1-Methylnaphthalene | 0.1 |
| 2-Methylnaphthalene | 8.2 |
| Anthracene | 9.1 |
| Benzo(a)anthracene | 1.0 |
| Biphenyl | 9.0 |
| Carbazole | 4.5 |
| Chrysene | 0.2 |
| Dibenzofuran | 4.5 |
| Fluoranthene | 11.6 |
| Fluorene | 7.7 |
| Indene | 0.5 |
| Napththalene | 5.4 |
| Phenanthrene | 28.1 |
| Pyrene | 9.1 |
| Quinoline | 0.4 |

The percentage weight may vary slightly if produced by distillation. This formulation may additionally have at least one of anthracene (9.1%) and benzo(a)anthracene (1%). The resultant mixture may be diluted in DMSO to the equivalent of 0.0014 mg/Mol. for use parenterally, intramuscularly, by injection to the spinal column, or converted to ingestible (pill) form. The formulation can also be diluted in ethanol and other alcohol carriers and delivered to the skin, bloodstream and intramuscularly as well as through the spinal column with alternative acceptable carriers. A preferred range of constituents for the formulation in weight percentages consists essentially of 0.4 to 0.6% acenapththene, 0.1 to 0.7% 1-methylnaphthalene, 0.8 to 1.4% 2-methylnaphthalene, 7.45 to 9.1% anthracene, 0.7 to 1.0% benzo(a)anthracene, 6.0 to 10% biphenyl, 3 to 5% carbazole, 0.2 to 0.9% chrysene, 3 to 5% dibenzofuran, 9 to 12% fluoranthene, 5 to 8% fluorene, 0.4 to 0.5% indene, 4 to 6% napththalene, 20 to 30% phenanthrene, 6 to 9% pyrene and 0.3 to 0.4% quinoline.

OncoX is a solution containing 5% of a coal tar formulation. The formulation is dissolved in a 15% DMSO/85% IPA solution. A preferred dose is 0.0114 milligrams/Mol. of solution, equivalent in potency to 23 micrograms of methotrexate, but may vary based on the condition treated and the severity of the disease. The invention may also be incorporated into lipid carriers for administration and targeted delivery to desired portions of the body. A formulation for OncoX is set forth below:

OncoX constituents

| Hydrocarbon | % by weight |
| --- | --- |
| Phenanthrene | 21.11 |
| Fluoranthene | 9.07 |
| Anthracene | 7.45 |
| Biphenyl | 6.83 |
| Pyrene | 6.54 |
| Fluorene | 5.58 |
| Naphthalene | 4.08 |
| Carbazole | 3.41 |
| Dibenzofuran | 3.25 |
| 2-methylnaphthalene | 1.33 |
| Chrysene | 0.87 |
| Benzo(a)anthracene | 0.76 |
| 1-methylnaphthalene | 0.63 |
| Acenaphthene | 0.46 |
| Indene | 0.40 |
| Quinoline | 0.30 |
| Tar Pitch | 27.93 |
| TOTAL | 100.00 |

Formulations for Delivery

The inventive compositions may be systemically administered via injection, typically by intravenous injection. Other injection routes, such as subcutaneous, intramuscular, or intraperitoneal, can also be used. Alternative means for systemic administration may include transmucosal and transdermal administration using penetrants such as bile salts, fusidic acids or other detergents. In treating multiple sclerosis, rheumatoid arthritis, metastatic cancer, lupus and ectopic pregnancy, the compositions may be delivered by injection or IV. The use of monoclonal antibodies is anticipated. In treating certain disorders, such as karposi sarcoma, administration generally may be topical or localized, in the form of salves, pastes, gels and the like.

If properly formulated in enteric or encapsulated formulations, oral administration may also be used. An additional method of administration is by dilution with acetic acid and DMSO (solvents) and a buffer solution and saline carriers at a dosage which will permit sufficient molecular release of the cytotoxins to provide a lengthy half-life. In this case, the anticipated high level of protein serum binding is used to advantage, acting as a dose-limiting and time-release method, much like many NSAID's.

The delivery of the inventive composition will now be described with reference to Examples 1 through 4.

EXAMPLE 1

Subcutaneous or Organ Implants for the Treatment of Cancer and Rheumatoid Arthritis OncoX is compatible with copolymers such as hydroxyethylmethacrylate (HEMA), hydroxypropyl-methacrylate (HPMA), trimethylolpropanetriethacrylate (TYMPTMA), and other polymers developed by Atrix Laboratories, Inc. and Hydrogel Sciences, Inc. These substances are formed into devices which serve as a reservoir drug release system governed by Fick's first law of diffusion. As an example, such hydrogel capsules may be filled with 10–60 mg of OncoX, a typical size being 3.5 mm in diameter and 30 mm in length with a wall thickness of about 0.5 mm. The implant is then heat sterilized and may be supplied for use in a hydrated state. Such implants may deliver a range of daily dosing levels. Other types of copolymers, such as those developed by Atrix Laboratories, Inc., can be formulated as liquids and injected into the IP cavity, muscle, organ, or lymph system where the liquid solidifies and time releases the cytotoxic agent. An example of dosing ranges is 220 ug/day, 110/ug/day or 55 ug/day and will vary depending on the age, health, and disease of the patient. Implants can remain active from one to several months, or more than a year, depending upon the release rate. Patients can be monitored during treatment by measuring serum concentrations of PSA and testosterone or other important markers depending on the disease.

EXAMPLE 2

Gel Formulations for Treating Restenosis

A pure gel formulation may be used for the treatment of restenosis to be applied to the arterial walls upon completion of angioplasty and possibly periodically thereafter. This is currently the practice with other medications and medical devices which currently excavate and topically medicate arterial plaque.

EXAMPLE 3

Post-surgical Cancer Treatment

A hydrogel dressing may be used involving a copolymer matrix structure which is spread throughout the surgical cavity upon removal of a tumor. By time release from the copolymer matrix, OncoX is diffused to adjacent tissue where invasion or metastatic cells are suspected. The matrix remains within the cavity and supports regrowth acting as a bio-latticework. OncoX may be administered in high doses followed by leucovorin rescue which, in combination with other chemotherapeutic agents, is effective in prolonging relapse-free survival in patients with non-metastatic osteosarcoma who have undergone surgical resection or amputation for a primary tumor.

EXAMPLE 4

Intravenous Delivery for the Treatment of Cancer, Rheumatoid Arthritis, Multiple Sclerosis Injection or IV administration by infusion may be accomplished with use of lipid-coated microspheres such as the technology developed by the U.S. government and Cavitation-Control Technology Inc. which are compatible with lipophilic agents and have demonstrated rapid tumor uptake and tumor diffusion in animal testing. An alternative method of delivery is the use of phospholipid encapsulation such as the technology developed by RTP Pharma. This system captures the drug at the core of a phospholipid sphere capable of carrying the drug in a "stealth" fashion through the bloodstream where it is recognized by tumor receptors as a cholesterol and endocytosed.

The invention, its utility and applications will now be described with reference to the following examples 5 through 9, it being understood that these examples are provided to illustrate the invention and are not limiting in nature.

EXAMPLE 5

A solution having 0.0114 mg/Mol. of the composition was assayed in a DHFR assay system specifically designed to measure methotrexate in blood and body fluids using a Tris-EDTA buffer at pH 7.6 containing NADPH and folate as substrate. Coal tar distillates were decolorized and dissolved in DMSO. The samples were then analyzed by the aforementioned DHFR assay system. It was found that coal tar distillates demonstrated a significant inhibitor effect equivalent to 17,000 and 23000 nM MTX. The presence of coal tar distillates in neoplastic cell cultures blocks the conversion of dihydrofolate to tetrahydrofolate.

EXAMPLE 6

Ectopic Pregnancy

For chemotherapeutic or ectopic pregnancy treatment, the mixture can be solubilized in DMSO or other suitable solvent, and diluted to a dosing of 0.0114 mg/Mol. of internal standard solution.

EXAMPLE 7

Rheumatoid Arthritis/Lupus

Treatment of rheumatoid arthritis typically utilizes a single dosing 70% lower, or 0.0003 mg/Mol., administered once or twice weekly depending upon the severity of the condition and patient response rate. For rheumatoid arthritis and lupus the dose may be given weekly whether by injection or oral administration.

EXAMPLE 8

Restenosis

OncoX may be used in a method of inhibiting vascular smooth muscle cell proliferation and vascular restenosis following angioplasty when formulated into a pharmaceutically acceptable carrier, including salts and solvates thereof. A 2-hour infusion of OncoX at the time of balloon angioplasty may reduce vessel wall-associated thrombin activity. It is contemplated that a second, delayed infusion may reduce restenosis by a greater extent than a single early infusion. The invention is useful therapeutically in the treatment of abrupt closure or restenosis in the context of angioplasty and would be administered in conventional formulations for systemic administration as is known in the art. Typical such formulations may be found, for example, in the text, *Remington's Pharmaceutical Sciences,* (Mack Publishing Co., Easton Pa., latest edition), incorporated herein by reference.

The appropriate dosage range selected by the physician depends on the choice of antagonist, the route of administration, the nature of the formulation, and the nature of the patient's illness. Suitable doses, however, are in the range of about 0.1–100 ug/kg of subject. There may be wide variations in the dosages in view of the differing efficiencies of various routes of administration. For example, oral administration may require higher doses than administration by intravenous injection. Variations in these dosage levels can be adjusted using standard empirical routines for optimization as is well understood in the art. For cancer treatment generally higher doses are used which are often administered intravenously or intramuscularly.

EXAMPLE 9

Neoplastic Diseases

Oral administration in tablet form is often preferred when low doses are being administered since absorption is rapid and effective serum levels are obtained. When injections are used, they may be given by the intramuscular, intravenous, intra-arterial or intrathecal routes. However, formulations containing benzyl alcohol must not be used for intrathecal or high dose therapy. Parenteral drug products should be inspected visually for particulate matter and discoloration prior to administration, whenever the solution and container permit.

For choriocarcinoma and similar trophoblastic diseases, OncoX may be administered orally or intramuscularly in doses of 5 to 30 mg daily for a five-day course. Such courses may be repeated for 3 to 5 times, with rest periods of one or more weeks interposed between courses, until any manifesting toxic symptoms subside. The effectiveness of therapy may be evaluated by 24 hour quantitative analysis of urinary chorionic gonadotropin (hCG). One to two courses of OncoX after normalization of hCG is usually recommended. Before each course of the drug careful clinical assessment is important. Cyclic combination therapy of OncoX with other antitumor drugs may be useful.

Since hydatidiform mole may precede choriocarcinoma, prophylactic chemotherapy with OncoX is recommended. Chorioadenoma destruens is considered to be an invasive form of hydatidiform mole. OncoX may be administered in these disease states in doses similar to those recommended for choriocarcinoma.

Leukemia: Acute lymphoblastic leukemia in children and young adolescents is the most responsive to chemotherapy. In young adults and older patients, clinical remission is more difficult to obtain and early relapse is more common.

OncoX alone or in combination with steroids may be used initially for induction of remission in acute lymphoblastic leukemias. Corticosteroid therapy, in combination with other antileukemic drugs or in cyclic combinations with OncoX also may be used. When used for induction, OncoX in doses of 3.3 mg/m$^2$ in combination with 60 mg/m$^2$ of prednisone, given daily, may be used over a period of 4 to 6 weeks. When remission is achieved and supportive care has produced general clinical improvement, maintenance therapy may be initiated, as follows: OncoX may be administered 2 times weekly either by mouth or intramuscularly in total weekly doses of 30 mg/m$^2$. It also may be given in doses of 2.5 mg/kg intravenously every 14 days. If and when relapse does occur, reinduction of remission can again be sought by repeating the initial induction regimen.

A variety of combination chemotherapy regimens may be used for both induction and maintenance therapy in acute lymphoblastic leukemia.

Meningeal Leukemia: In treating meningeal leukemia, OncoX may be administered intrathecally. Preservative free OncoX may be diluted to a concentration of 1 mg/mL in an appropriate sterile, preservative free medium such as 0.9% Sodium Chloride Injection, USP. The cerebrospinal fluid volume is dependent on age and not on body surface area. The CSF is at 40% of the adult volume at birth and reaches the adult volume in several years. The following dosage regimen is based on age instead of body surface area:

| AGE | DOSE (mg) |
|---|---|
| Less than 1 | 6 |
| 1 | 8 |
| 2 | 10 |
| 3 or older | 12 |

Because the CSF volume and turnover may decrease with age, a dose reduction may be indicated in elderly patients.

For the treatment of meningeal leukemia, intrathecal OncoX may be given at intervals of 2 to 5 days. OncoX may be administered until the cell count of the cerebrospinal fluid returns to normal. At this point an additional dose may be used. For prophylaxis against meningeal leukemia, the dosage is the same as for treatment except for the intervals of administration, which can be ascertained by the physician as is known in the field. Untoward side effects may occur with any given intrathecal injection, such that systemic antileukemic therapy with the drug should be appropriately adjusted, reduced, or discontinued in the presence of side effects.

Lymphomas: In Burkitt's tumor, Stages I–II, a dosage of OncoX is 10 to 25 mg/day orally for 4 to 8 days. In Stage III, OncoX may be given concomitantly with other antitumor agents. Treatment in all stages may consist of several courses of the drug interposed with 7 to 10 day rest periods. Lymphosarcomas in Stage III may respond to combined drug therapy with OncoX given in doses of 0.625 to 2.5 mg/kg daily.

Mycosis Fungoides: Dosage may be 2.5 to 10 mg daily by mouth for weeks or months. Dose levels of the drug and adjustment of dose regimen may be guided by patient response and hematologic monitoring. OncoX may also be given intramuscularly in doses of 50 mg once weekly or 25 mg 2 times weekly.

Osteosarcoma: An effective adjuvant chemotherapy regimen requires the administration of several cytotoxic chemotherapeutic agents. In addition to high-dose OncoX with leucovorin rescue, these agents may include doxorubicin, cisplatin, and the combination of bleomycin, cyclophosphamide and dactinomycin (BCD) in the doses and schedule shown in the table below. The starting dose for high dose OncoX treatment may be 12 grams/m$^2$. If this dose is not sufficient to produce a peak serum OncoX concentration of 1,000 micromolar ($10^{-3}$ mol/L) at the end of the OncoX infusion, the dose may be escalated to 15 grams/m$^2$ in subsequent treatments. If the patient is vomiting or unable to tolerate oral medication, leucovorin may be given IV or IM at the same dose and schedule.

| | |
|---|---|
| Dose (OncoX) | 12 g/m$^2$ IV as 4 hour infusion (starting dose) |
| Treatment Week After Surgery | 4, 5, 6, 7, 11, 12, 15, 16, 29, 30, 44, 45 |

It is understood that the embodiments described herein are merely exemplary and that a person skilled in the art may make variations and modifications without departing from the spirit and scope of the invention. All such variations and modifications are intended to be included within the scope of the appended claims.

I claim:

1. A method for treating disorders responsive to DHFR inhibition comprising administering to a patient in need of such treatment a therapeutically-effective amount of a composition comprising a formulation comprising 0.4 to 0.6% acenaphthene, 0.1 to 0.7% 1-methylnaphthalene, 0.8 to 1.4% 2-methylnaphthalene, 7.45 to 9.1% anthracene, 0.7 to 1.0% benzo(a)anthracene, 6.0 to 10% biphenyl, 3 to 5% carbazole, 0.2 to 0.9% chrysene, 3 to 5% dibenzofuran, 9 to 12% fluoranthene, 5 to 8% fluorine, 0.4 to 0.5% indene, 4 to 6% napththalene, 20 to 30% phenanthrene, 6 to 9% pyrene and 0.3 to 0.4% quinoline.

2. The method of claim 1 in which the formulation comprises 0.46% acenaphthene, 0.63% 1-methylnaphthalene, 1.3% 2-methylnaphthalene, 7.45% anthracene, 0.76% benzo(a)anthracene, 6.83% biphenyl, 3.41% carbazole, 0.87% chrysene, 3.25% dibenzofuran, 9.07% fluoranthene, 5.58% fluorine, 0.4% indene, 4.08% napththalene, 21.11% phenanthrene, 6.54% pyrene and 0.3% quinoline.

3. The method according to claim 1 wherein the composition is administered to the patient intratumorally, by organ implantation, transmucosally, transdermally or by intravenous, subcutaneous, intramuscular, oral, topical, or intraperitoneal injection.

4. A pharmaceutical composition comprising a hydrogel capsule containing a formulation comprising 0.4 to 0.6% acenaphthene, 0.1 to 0.7% 1-methylnaphthalene, 0.8 to 1.4% 2-methylnaphthalene, 7.45 to 9.1% anthracene, 0.7 to 1.0% benzo(a)anthracene, 6.0 to 10% biphenyl, 3 to 5% carbazole, 0.2 to 0.9% chrysene, 3 to 5% dibenzofuran, 9 to 12% fluoranthene, 5 to 8% fluorine, 0.4 to 0.5% indene, 4 to 6% napththalene, 20 to 30% phenanthrene, 6 to 9% pyrene and 0.3 to 0.4% quinoline and a copolymer.

5. The pharmaceutical composition of claim 4 in which the copolymer is selected from hydroxyethylmethacrylate, hydroxypropyl-methacrylate, and trimethylolpropanetriethacrylate.

6. A method for treating soft tissue tumor or bony metastatic cancer in a mammal comprising administering to said mammal a therapeutically effective amount of a composition comprising 0.4 to 0.6% acenaphthene, 0.1 to 0.7% 1-methylnaphthalene, 0.8 to 1.4% 2-methylnaphthalene, 7.45 to 9.1% anthracene, 0.7 to 1.0% benzo(a)anthracene, 6.0 to 10% biphenyl, 3 to 5% carbazole, 0.2 to 0.9% chrysene, 3 to 5% dibenzofuran, 9 to 12% fluoranthene, 5 to 8% fluorine, 0.4 to 0.5% indene, 4 to 6% napththalene, 20 to 30% phenanthrene, 6 to 9% pyrene and 0.3 to 0.4% quinoline.

7. The method according to claim 6 wherein said cancer is of the prostate, liver, testes, breast, glands, or epidermis, or prostate or breast cancers metastatic to bone.

8. The method according to claim 6 further comprising administering at least one chemotherapeutic agent.

9. A pharmaceutical composition comprising a hydrogel dressing comprising a formulation comprising 0.4 to 0.6% acenaphthene, 0.1 to 0.7% 1-methylnaphthalene, 0.8 to 1.4% 2-methylnaphthalene, 7.45 to 9.1% anthracene, 0.7 to 1.0% benzo(a)anthracene, 6.0 to 10% biphenyl, 3 to 5% carbazole, 0.2 to 0.9% chrysene, 3 to 5% dibenzofuran, 9 to 12% fluoranthene, 5 to 8% fluorine, 0.4 to 0.5% indene, 4 to 6% napththalene, 20 to 30% phenanthrene, 6 to 9% pyrene and 0.3 to 0.4% quinoline and a copolymer.

10. A pharmaceutical composition comprising a lipid carrier containing a formulation comprising 0.4 to 0.6% acenaphthene, 0.1 to 0.7% 1-methylnaphthalene, 0.8 to 1.4% 2-methylnaphthalene, 7.45 to 9.1% anthracene, 0.7 to 1.0% benzo(a)anthracene, 6.0 to 10% biphenyl, 3 to 5% carbazole, 0.2 to 0.9% chrysene, 3 to 5% dibenzofuran, 9 to 12% fluoranthene, 5 to 8% fluorine, 0.4 to 0.5% indene, 4 to 6% napththalene, 20 to 30% phenanthrene, 6 to 9% pyrene and 0.3 to 0.4% quinoline.

11. The pharmaceutical composition according to claim 10 further comprising lipid-coated microspheres containing said formulation.

12. The pharmaceutical composition according to claim 10 further comprising a phospholipid sphere containing said formulation.

* * * * *

UNITED STATES PATENT AND TRADEMARK OFFICE
CERTIFICATE OF CORRECTION

PATENT NO. : 6,337,337 B1
APPLICATION NO. : 09/390609
DATED : January 8, 2002
INVENTOR(S) : Carol J. Buck It is certified that error appears in the above-identified patent and that said Letters Patent is hereby corrected as shown below:

Column 9, line 10 claim 1 "fluorine" should be changed to --fluorene--

Column 9, line 18 claim 2 "fluorine" should be changed to --fluorene--

Column 9, line 32 claim 4 "fluorine" should be changed to --fluorene--

Column 10, line 7 claim 6 "fluorine" should be changed to --fluorene--

Column 10, line 21 claim 9 "fluorine" should be changed to --fluorene--

Column 10, line 30 claim 10 "fluorine" should be changed to --fluorene--

Signed and Sealed this

Eighteenth Day of March, 2008

JON W. DUDAS
*Director of the United States Patent and Trademark Office*